United States Patent [19]

Hanamura et al.

[11] Patent Number: 5,565,938
[45] Date of Patent: Oct. 15, 1996

[54] OPHTHALMOLOGIC APPARATUS HAVING IMPROVED DISPLAY CAPABILITY

[75] Inventors: Yoshihiko Hanamura; Takeyuki Kato, both of Tokyo, Japan

[73] Assignee: Kabushiki Kaisha Topcon, Tokyo, Japan

[21] Appl. No.: 340,362

[22] Filed: Nov. 14, 1994

[30] Foreign Application Priority Data

Nov. 15, 1993 [JP] Japan ..................................... 5-285255

[51] Int. Cl.$^6$ ..................................................... A61B 3/14
[52] U.S. Cl. .......................................... 351/206; 351/213
[58] Field of Search ..................................... 351/205, 206, 351/213, 221

[56] References Cited

U.S. PATENT DOCUMENTS 5,118,179  6/1992  Sano et al. ................................. 351/206
5,287,129  2/1994  Sano et al. ................................. 351/213

FOREIGN PATENT DOCUMENTS

4226625  8/1992  Japan ....................................... 351/221

*Primary Examiner*—William L. Sikes
*Assistant Examiner*—James A. Dudek
*Attorney, Agent, or Firm*—Finnegan, Henderson, Farabow, Garrett & Dunner, L.L.P.

[57] ABSTRACT

Illumination light emitted by an illuminating light source, such as a halogen lamp or xenon lamp, is projected onto a subject's eye via an illuminating optical system placed in the main body of an ophthalmologic apparatus, while light reflected by the eye is guided to either of a color television camera and an infra-red television camera mounted in the body via an observing and photographing optical system and, in accordance with video signals delivered by the television cameras, an image of the eye is displayed on a color liquid crystal monitor mounted in the main body.

11 Claims, 5 Drawing Sheets

FIG.6 (b)  PRIOR ART

OPHTHALMOLOGIC APPARATUS HAVING IMPROVED DISPLAY CAPABILITY

BACKGROUND OF THE INVENTION

1. Field of the Invention

This invention relates to an ophthalmologic apparatus of which a main body is provided with an image displaying device capable of displaying an image of a subject's eye captured by a television camera which is an electric pickup unit.

2. Description of the Prior Art

Figure 6A:
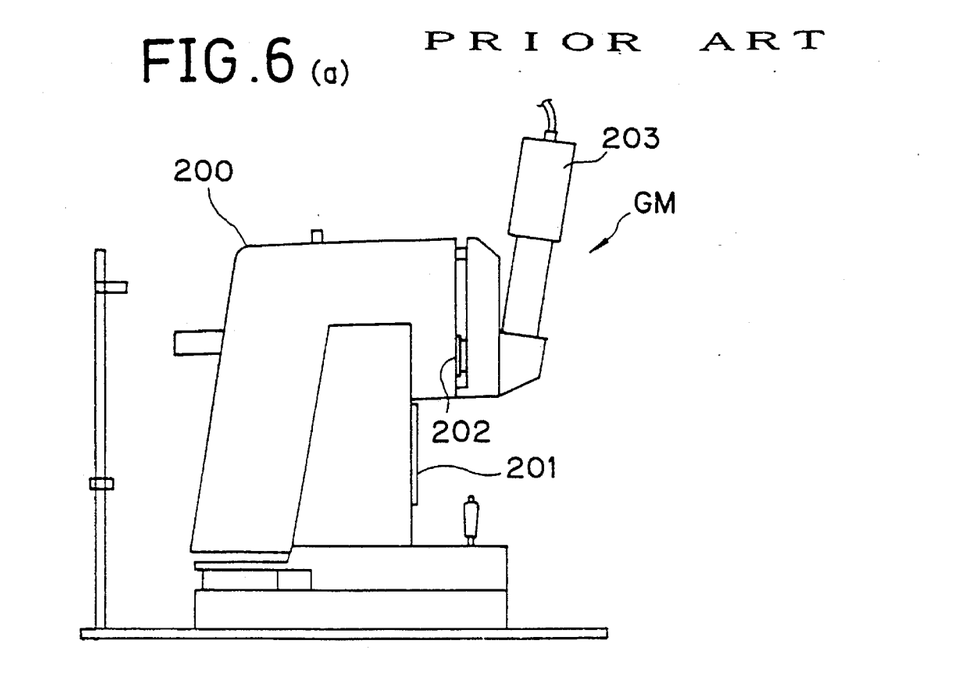
FIG. 6(a) is a side view of a conventional ophthalmologic apparatus and FIG. 6(b) is a right side view of the ophthalmologic apparatus of FIG. 6(a).
Figure 6B:
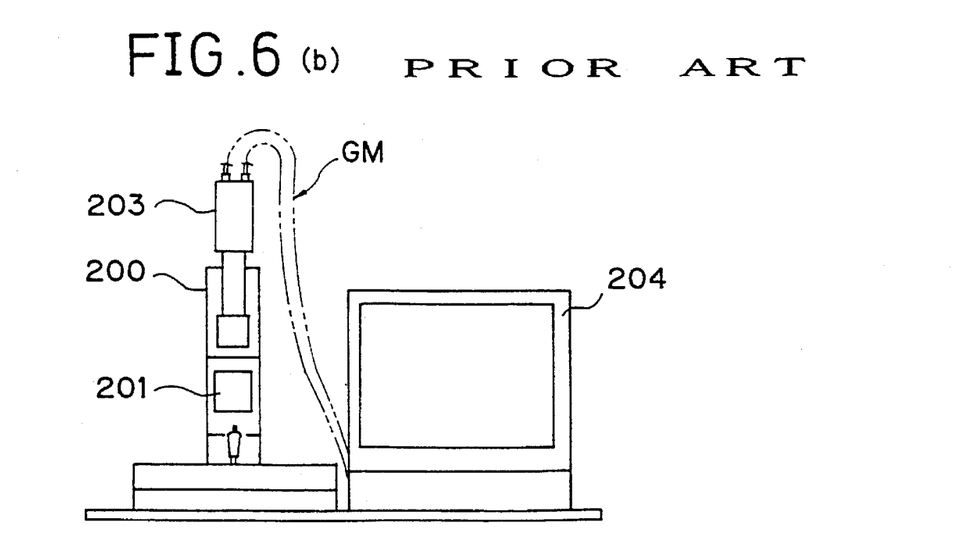

As this type of ophthalmologic apparatus, a fundus camera GM is known as shown in FIGS. 6(a) and 6(b). In the fundus camera GM, infra-red light is guided to the fundus of a subject's eye via an illuminating optical system to illuminate the fundus, while infra-red light reflected by the fundus is guided to an infra-red television camera sensitive to infra-red light via an observing and photographing optical system and then a fundus image of the eye captured by the television camera is displayed on a black-and-white TV monitor 201 mounted in the body 200 of the fundus camera GM.

However, since an image displaying means mounted in the body 200 is the black-and-white TV monitor 201, a color image of the fundus cannot be displayed thereon. In order to view a color fundus image, it is necessary to mount a color television camera 208 on a camera mount 202 of the body 200 and guide visible light to the fundus via the illuminating optical system to illuminate the fundus. The visible light is reflected by the fundus and is guided to the color television camera 203 via the observing and photographing optical system, and then an image picked up by the color television camera 203 is displayed on the screen of a color TV monitor 204 (see FIG. 6(b)) separated from the camera body 200.

As mentioned above, in order to observe a color image of the fundus, a color TV monitor separated from the fundus camera GM and, therefore, a wide space for it have been conventionally required. Further, disadvantageously, cords connecting the color TV monitor 204 with the camera body 200 are liable to be confusingly placed or entangled with each other.

Further, cases occur in which, when photographed in a dark room, a harmful influence is exerted on the observation and photography of the fundus because the two TV monitors each as an image displaying device produce an illumination effect.

SUMMARY OF THE INVENTION

It is therefore an object of the present invention to provide an ophthalmologic apparatus in which an image displaying device capable of displaying black-and-white fundus images generated by infra-red photography and color fundus images generated by color photography is mounted in the main body of the ophthalmologic apparatus and, by avoiding use of a color TV monitor that is separated from the body, an empty space is effectively utilized, and in addition, harmful illumination light caused by the separated monitor is extinguished.

To achieve the object, the ophthalmologic apparatus according to the present invention includes a visible illuminating light source mounted in the main housing body of the apparatus, an infra-red illuminating light source mounted in the body, an illuminating optical system for projecting light emitted by the visible and infra-red illuminating light sources onto a subject's eye, a color electronic image pickup means sensitive to light included in a visible wavelength range, an infra-red electronic image pickup means sensitive to light included in an infra-red wavelength range, a color photographic optical system for guiding visible light reflected by the eye to the color electronic image pickup means and forming an image, an infra-red photographic optical system for guiding infra-red light reflected by the eye to the infra-red electronic image pickup means and forming an image, a color image displaying device which is mounted in the main body and displays an ophthalmologic image in accordance with video signals sent from each of the color and infra-red electronic image pickup means, and a control circuit by which the video signals sent from the color and infra-red electronic image pickup means are shifted from one to the other to input the video signals to the color image displaying device so that color and infra-red ophthalmologic images are alternately displayed on the color image displaying device.

The control circuit is also arranged so that the infra-red illuminating light source is selected and turned on to project infrared illumination light onto the eye when the ophthalmologic apparatus is actuated, and then infra-red light reflected by the eye is guided to the infra-red electronic image pickup means and thereby an infra-red ophthalmological image is displayed on the color image displaying device.

The infra-red illuminating light source includes an illuminating light source for observation emitting light in an infra-red wavelength range and an exciter filter for infra-red fluorescence which is inserted into an optical path by a driving means controlled by the control circuit and transmits infra-red light having wavelengths for infra-red fluorescence excitation which is included in the illuminating light source for observation.

Further, the control circuit is arranged so that the visible illuminating light source is selected and turned on to project visible illumination light onto the eye when a photographic switch is turned on, and then visible light reflected by the eye is guided to the color electronic image pickup means via the color photographic optical system and a color ophthalmological image delivered by the color electronic image pickup means is displayed on the color image displaying device.

Further, the control circuit is arranged so that the illuminating light source for observation stops or lessen the light emission when the photographic switch is turned on and, at the same time, the exciter filter for infra-red fluorescence is moved out of the optical path, and then a xenon lamp which is the visible illuminating light source is switched on to project visible illumination light onto the eye, thereafter visible light reflected by the eye is guided to the color electronic image pickup means via the color photographic optical system, so that a color ophthalmologic image delivered from the color electronic image pickup means is displayed on the color image displaying device.

The visible illuminating light source includes a photographic illuminating light source which emits light in a visible wavelength range and an exciter filter for visible fluorescence which is inserted into the optical path by the driving means controlled by the control circuit and transmits light having wavelengths for visible fluorescence excitation which is included in the photographic illuminating light source.

The color image displaying device is a color liquid crystal monitor which is forward and backward tiltably mounted in the main body and is tilted forward and backward by a monitor driving means controlled by the control circuit. The monitor driving means is a pulse motor.

DETAILED DESCRIPTION OF THE PREFERRED EMBODIMENT

The embodiment of the present invention will be hereinafter described with reference to the attached drawings.
General Arrangement In FIGS. 3(a) and 3(b), reference numeral 100 designates a fundus camera according to the present invention. The fundus camera 100 includes a base 101, a table 102 fixed to the base 101, a movable table 103 mounted on the fixed table 102. As shown in FIG. 4, a pair of guide rails 104 and 104 are mounted on the fixed table 102. The movable table 103 is provided with a rotary shaft 105 and wheels 106 and 106. The rotary shaft 105 lies between the guide rails 104 and 104 and is capable of rotating about its axis. The wheels 106 and 106 are fixed to the respective ends of the rotary shaft 105 and roll along the guide rails 104 and 104. Engagement holes, not shown, are formed in the guide rails 104 and 104 at equal pitches in a longitudinal direction of the rails. The wheels 106 and 106 have cone-shaped engagement pins, not shown, which engage with the engagement holes of the guide rails.

The movable table 103 is laterally movably supported by the rotary shaft 105. A rotary encoder (fore-and-aft position detecting means) 107 is disposed between the movable table 103 and the rotary shaft 105. The rotary encoder 107 detects a moving distance of the table 103 in a fore-and-aft direction.

Figure 3:
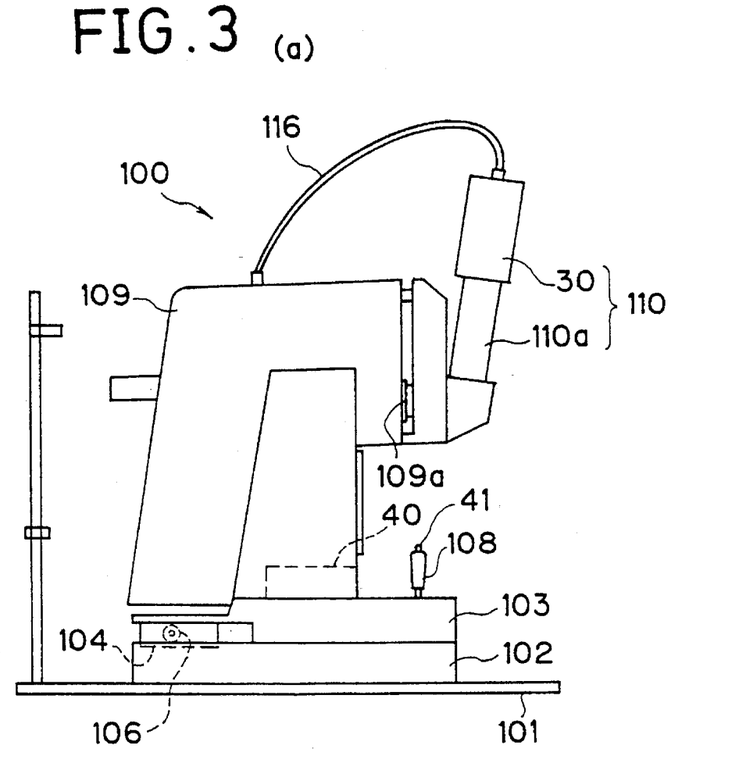
FIG. 3(a) is a side view of the ophthalmologic apparatus and FIG. 3(b) is a right side view of the ophthalmologic apparatus of FIG. 3(a).
Figure 4:
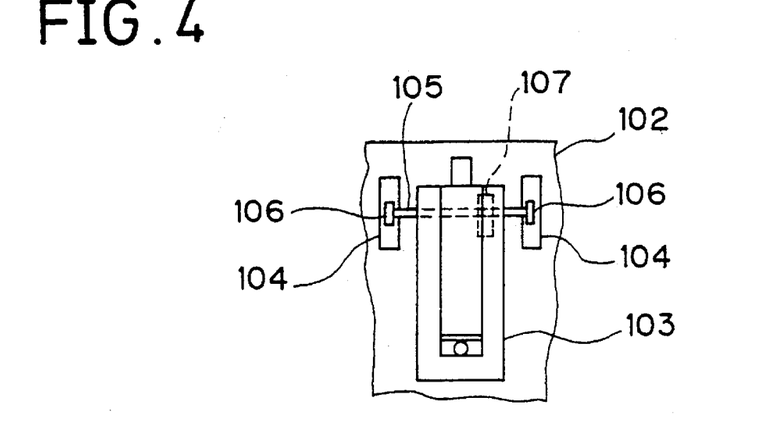
FIG. 4 is a segmentary view showing the construction of a movable table shown in FIGS. 3(a) and 3(b).

As shown in FIGS. 3(a) and 3(b), the fundus camera 100 also includes a joy stick 108 which is mounted on the movable table 103 and is tilted in an optional direction so that the movable table 103 may be moved in the direction. A photographic switch 41 is mounted on the joy stick 108.

The fundus camera 100 further includes a camera body (main housing body of the ophthalmologic apparatus) 109 fixed to the movable table 103 and a color image pickup device 110 mounted on a camera mount 109a of the camera body 109. The color image pickup device 110 includes a housing portion 110a for containing optical parts which convey video signals sent from optical systems placed in the camera body 109. A color television camera 30, hereinafter referred to, is connected to the housing portion 110a.

Optical Systems in the Camera Body

Figure 1:
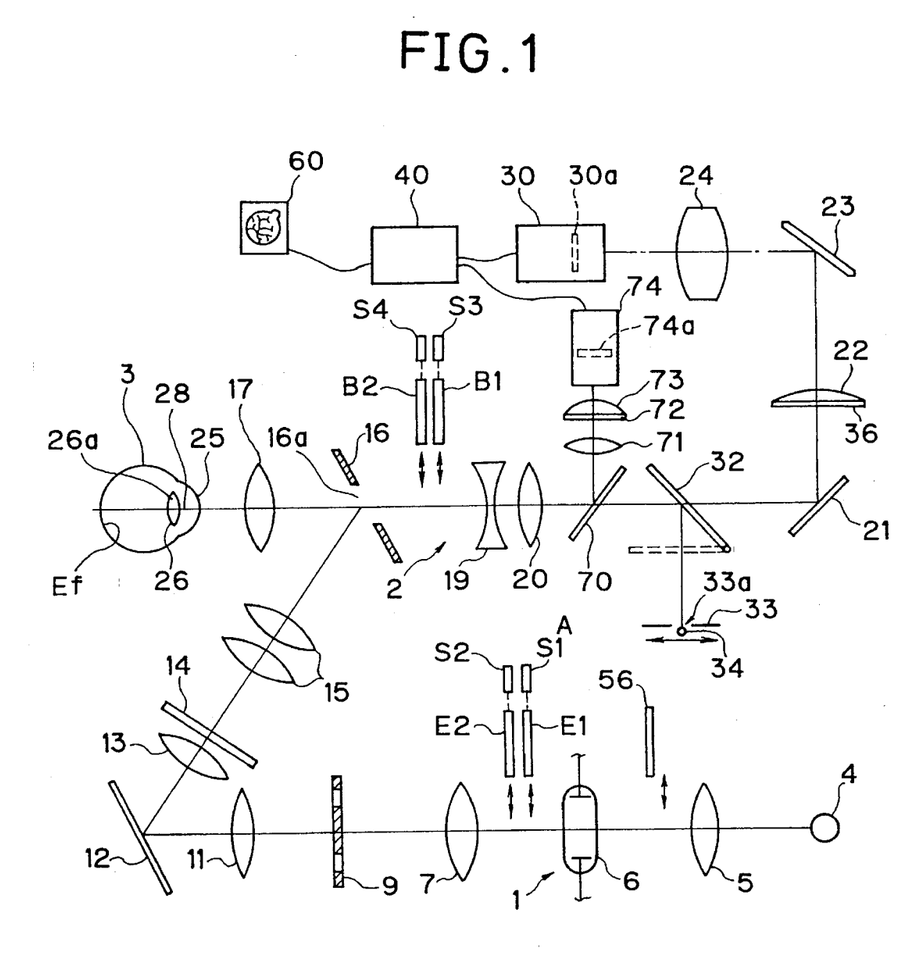
FIG. 1 is a schematic view showing optical systems of an ophthalmologic apparatus according to the present invention.

In FIG. 1, reference numeral 1 designates an illuminating optical system in the camera body 109, reference numeral 2 designates an observing and photographing optical system in the camera body 109, and reference numeral 3 designates a subject's eye.
Illuminating Optical System The illuminating optical system 1 consists of an illuminating optical system for observation and an illuminating optical system for photography.

The illuminating optical system for photography includes a xenon lamp (illuminating light source for photography) 6, a condenser lens 7, a ring-shaped diaphragm 9, a relay lens 11, a reflecting mirror 12, a relay lens 13, a black spot plate 14 (an optical member for intercepting harmful light reflected by an objective lens), a relay lens 15, a perforated mirror 16, and an objective lens 17 in order of mention. Illumination light for photography emitted by the xenon lamp 6 is projected onto a fundus Ef of the eye 3 via the optical members ranging from the condenser lens 7 to the objective lens 17.

An exciter filter E1 for visible fluorescence and an exciter filter E2 for infra-red fluorescence are disposed between the xenon lamp 6 and the condenser lens 7. The exciter filters E1 and E2 are inserted or extracted into or from an optical path of the optical system by means of solenoids (first filter driving means) S1 and 82, respectively.

The illuminating optical system for observation includes a halogen lamp (illuminating light source for observation) 4, a condenser lens 5, and the optical members ranging from the condenser lens 7 to the objective lens 17. Illumination light for observation emitted by the halogen lamp 4 is projected onto the fundus Ef via the optical members from the condenser lens 5 to the objective lens 17.
Observing and Photographing Optical System The observing and photographing optical system 2 consists of a color photographic optical system and an infra-red photographic optical system.

The color photographic optical system consists of an inner optical system disposed in the camera body 109 and an outer optical system disposed in the color image pickup device 110 connected to the camera body 109. The inner optical system includes the objective lens 17 facing the eye 3, a focusing lens 19, and an image-formation lens 20. The outer optical system includes a mirror 21, a mask 36, a field lens 22 disposed at a point conjugate with the fundus Ef, a reflecting mirror 23, a relay lens 24, and a color television camera (color electronic image pickup means) 30. In FIG. 1, 30a designates a color area CCD of the color television camera 30.

The infra-red photographic optical system includes the objective lens 17, the focusing lens 19, the image-formation lens 20, a dichroic mirror 70 disposed between the image-formation lens 20 and the mirror 21, a lens 71, a mask 72, a field lens 73, and a television camera 74 for infra-red photography (infra-red electronic image pickup means) sensitive to infra-red light. The dichroic mirror 70 serves to reflect light having wavelengths in the infra-red region of the electromagnetic spectrum and transmit light having wavelengths in the visible region of the electromagnetic spectrum. In FIG. 1, 74a designates an area CCD of the television camera 74 sensitive to infra-red light.

A barrier filter B1 for visible fluorescence and a barrier filter B2 for infra-red fluorescence are disposed between the perforated mirror 16 and the focusing lens 19. The barrier filters B1 and B2 are inserted or extracted into or from an optical path of the optical system by means of solenoids (second filter driving means) S3 and S4, respectively.

Accordingly, a color fundus image is formed on the area CCD 30a of the color television camera 30 by visible light which is reflected by the fundus Ef and passes through the optical members from the objective lens 17 to the image-formation lens 20, the mirror 21, the mask 36, the field lens 22, the reflecting mirror and the relay lens 24.

On the other hand, an infra-red fundus image is formed on the area CCD 74a of the television camera (infra-red electronic image pickup means) 74 by infra-red light which is reflected from the fundus Ef and passes through the optical members from the objective lens 17 to the image-formation lens 20, the dichroic mirror 70, the lens 71, the mask 72, and the field lens 73.

When the exciter filters E1 and E2 are out of the optical path, the halogen lamp 4 and the xenon lamp 6, by itself, serve as a visible illuminating light source for visible color observation and a visible illuminating light source for visible color photography, respectively. Further, when the exciter filter E1 is inserted in the optical path, the halogen and xenon lamps 4 and 6, together with the exciter filter E1, serve each as a visible illuminating light source for projecting visible illumination light in a specific wavelength range for visible fluorescence excitation. Further, when the exciter filter E2 is inserted in the optical path, the halogen and xenon lamps 4 and 6, together with the exciter filter E2, serve each as an infra-red illuminating light source for projecting infra-red illumination light in a specific wavelength range for infra-red fluorescence excitation.

Eye-Fixation Optical System

An eye-fixation optical system A includes a half mirror 82 insertably and retractably disposed between the image-formation lens 20 and the mirror 21, an eye-fixation mask 88 disposed at a point conjugate with the fundus Ef and having a small hole 83a as a target on which the subject's eye is fixed, and a light source 84 for eye-fixation, such as a light emitting diode, facing the small hole 33a. The mask 38 and the light source 34 are mounted on a target driving device 85, not shown, such as an X-Y table electrically driven and controlled by a pulse motor or the like.

Color Image Displaying Device

Figure 5:
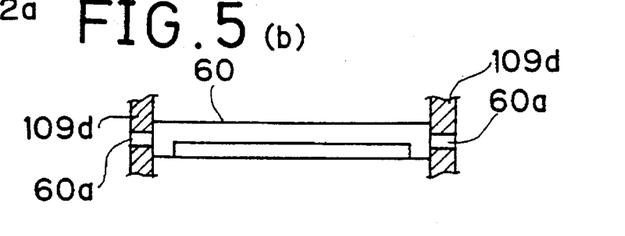
FIG. 5(a) illustrates the construction of a tiltable color liquid crystal monitor of FIG. 3(b)
FIG. 5(b) is a sectional view of a portion for supporting the color liquid crystal monitor of FIG. 5(a)
FIG. 5(c) is a side view of a pulse motor of FIG. 5(a).

In FIG. 3(b), 60 designates a panel-like color liquid crystal monitor (color liquid crystal display). As shown in FIGS. 3(a) and 3(b), the color liquid crystal monitor 60, i.e., color image displaying device is mounted in the back (operator's side) of the camera body 109. As shown in more detail in FIG. 5(a), the color liquid crystal monitor 60 is fit in an opening 109c formed in the back wall 109b of the camera body 109. Short cylindrical rods 60a and 60a integrated with the lower side parts of the monitor 60 are rotatably placed in the side walls 109d and 109d enclosing the opening 109c. As shown in FIGS. 5(a) and 5(c), the camera body 109 includes a stationary pulse motor (motor driving means) 111 close to the color liquid crystal monitor 60, a reducing gear 112 interlocking with the pulse motor 111, an arm 113 fixed to an output shaft 112a of the reducing gear 112, and a movable link 114 of which ends are connected to the arm 113 and the back of the liquid crystal monitor 60. In FIG. 5(a), 115 designates an operator's eye.

Control Circuit

Figure 2:
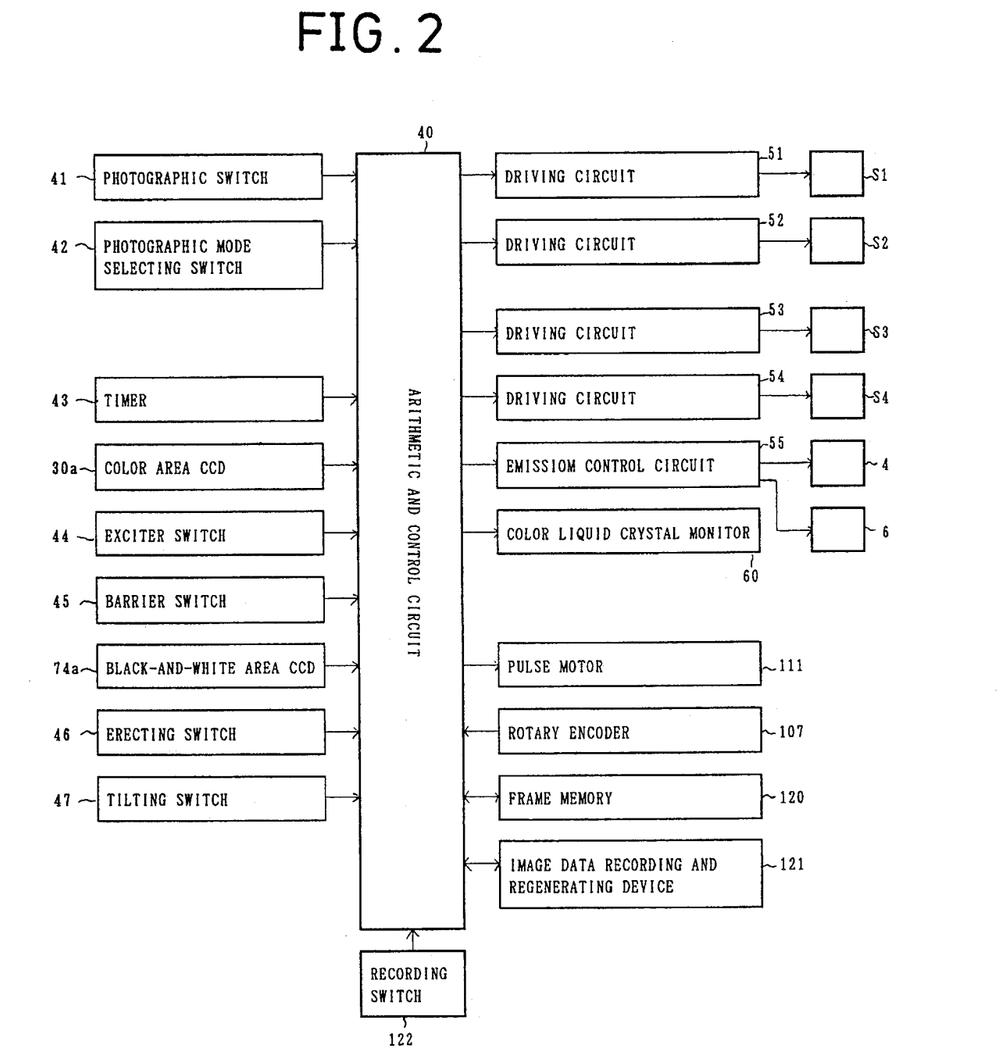
FIG. 2 is a control circuit diagram of the ophthalmologic apparatus having the optical systems of FIG. 1.

The fundus camera further includes an arithmetic and control circuit 40 shown in FIGS. 1 and 2. Signals are input to the arithmetic and control circuit 40 from a photographic switch 41, a photographic mode selecting switch 42, a timer switch 43, an exciter switch 44, a barrier switch 45, a monitor erecting switch 46, a monitor tilting switch 47, a rotary encoder 107, and so on.

The arithmetic and control circuit 40 drives and controls the solenoids S1–S4 via driving circuits 51–54 and, in addition, controls an emission control circuit 55.

The arithmetic and control circuit 40 further drives and controls the pulse motor 111 in accordance with signals transmitted from the erecting and tilting switches 46 and 47 and the rotary encoder 107. In detail, when receiving a signal from the erecting switch 46, the arithmetic and control circuit 40 starts the pulse motor 111 in normal rotation so that the arm 113 shown in FIG. 5(a) can move clockwise to turn the upper part of the liquid crystal monitor 60 backward (i.e., toward the operator's eye 115) and erect the monitor 60, whereas, when receiving a signal from the tilting switch 47, the arithmetic and control circuit 40 reverses the pulse motor 111 so that the arm 113 can move counterclockwise to turn the upper part of the liquid crystal monitor 60 forward and tilt the monitor 60.

Further, when the camera body 109 is moved forward (i.e., toward the subject), the arithmetic and control circuit 40 detects an output delivered by the rotary encoder 107 and starts the pulse motor 111 in normal rotation so that the arm 113 can move clockwise to turn the upper part of the liquid crystal monitor 60 backward (i.e., toward the operator's eye 115) and erect the monitor 60. On the other hand, when the camera body 109 is moved backward, the arithmetic and control circuit 40 detects an output delivered by the rotary encoder 107 and reverses the pulse motor 111 so that the arm 113 can move counterclockwise to turn the upper part of the liquid crystal monitor 60 forward and tilt the monitor 60. An erected or tilted quantity of the color liquid crystal monitor 60 is continuously resulated in accordance with a forward or backward moving quantity of the camera body 109.

Under this control, the panel-like color liquid crystal monitor 60 mounted in the camera body 109 can be tilted forward or backward.

To the arithmetic and control circuit 40 are connected the area CCD 30a of the color television camera 30 and the area CCD 74a of the television camera 74 for infra-red photography as well as the liquid crystal monitor 60. In FIGS. 3(a) and 3(b), 116 and 117 designate cords for connecting the color television camera 30 to the arithmetic and control circuit 40 placed in the camera body 109.

The photographic mode selecting switch 42 selects any one from a visible color electronic photographic mode, a visible fluorescence electronic photographic mode, an infra-red electronic photographic mode, an infra-red fluorescence electronic photographic mode, etc.

In addition, a frame memory 120 and an image data recording and regenerating device 121 are connected to the arithmetic and control circuit 40. When the photographic switch 41 is turned on to pick up a fundus image by means of the television cameras 30 and 74, the frame memory 120 temporarily stores image signals, which are treated as still image signals, delivered from the area CCDs 34a and 74a of the television cameras 30 and 74. The arithmetic and control circuit 40 causes the fundus image stored in the frame memory 120 to be displayed on the screen of the color liquid crystal monitor 60. The operator (photographer) observes the displayed fundus image and determines whether the fundus was photographed in good condition or not. If in good condition, the operator turns on a recording switch 122, so that the arithmetic and control circuit 40 causes data about the fundus image temporarily stored in the frame memory 120 to be recorded in the image data recording and regenerating device 121.

The image data recording and regenerating device 121 is, for example, a video recorder, a still video recorder, an optical disk, a hard disk, a floppy disk, or the like. The video recorder is usually used to record a fluorescent image of the fundus as a motion image and is also used to record a still image.

Other Functions of the Arithmetic and Control Circuit 40

A description will now be given of the other functions of the arithmetic and control circuit 40 together with its action.

Non-Mydriasis Mode (1) Initial State (illumination state in non-mydriasis)

Usually, when a power switch (not shown) of the fundus camera is turned on regardless of whether the filters E1, E2, B1, and B2 are inserted in the optical paths or not, the arithmetic and control circuit 40 is actuated and initialized. After that, the arithmetic and control circuit 40 causes the solenoids S1, S2, S3, and S4 to extract the filters E1, B1, and B2 from the respective optical paths and insert the exciter filter E2 into the optical path.

The arithmetic and control circuit 40 then regulates the emission control circuit 55 to emit light from the halogen lamp 4. In the initial state, since it is undetermined whether the fundus is observed and photographed in a non-mydriasis mode or in a mydriasis mode, the halogen lamp 4 is, for safety, controlled not to emit visible light.

(2) Infra-red Observation and Visible Color Photography

Infra-red Observation

Accordingly, infra-red light included in the illumination light of the halogen lamp 4 passes through the exciter filter E2 and is projected onto the eye via the illuminating optical system 1, so that the fundus can be observed in the state of non-mydriasis.

Infra-red light reflected by the fundus is guided to the field lens 73 via the objective lens 17, the focusing lens 19, the image-formation lens, the dichroic mirror 70, the lens 71, and the mask 72 and forms a fundus image on the field lens 73.

The fundus image formed on the field lens 73 is conveyed to the area CCD 74a of the television camera 74 for infra-red photography and is displayed in the form of a monochromatic image and in real time on the screen of the color liquid crystal monitor 60 via the arithmetic and control circuit 40. Thus, the non-mydriasis observation of the fundus is carried out.

In this state, the operator carries out the alignment and focusing of the observing and photographing optical system 2 with respect to the fundus.

Visible Color Photography

When completing the alignment and focusing, the photographic switch 41 is turned on, and then the arithmetic and control circuit 40 causes the halogen lamp 4 to stop or lower the emission and causes the xenon lamp 6 to emit light. The illumination light emitted by the xenon lamp 6 is projected onto the fundus via the illuminating optical system 1.

Visible light reflected by the fundus is guided to the area CCD 30a of the television camera 30 for visible photography via the optical members ranging from the objective lens 17 to the relay lens 24 and forms a visible image thereon. The visible image formed on the area CCD 30a is then displayed on the screen of the color liquid crystal monitor 60.

(3) Infra-red Fluorescent Photography

In the case of infra-red fluorescent photography, while focusing is carried out with respect to the fundus, ICG (indocyanin green) which is a fluorescent agent is injected into a vein of the subject.

Before carrying out the focusing, the infra-red fluorescence photographic mode is first selected by the photographic mode selecting switch 42, and then the exciter switch 44 is pushed. Thereby, the arithmetic and control circuit 40 actuates the driving circuit 52 in order to drive the solenoid S2 and insert the exciter filter E2 into the optical path.

Likewise, when the barrier switch 45 is pushed, the arithmetic and control circuit 40 actuates the driving circuit 54 in order to drive the solenoid S4 and insert the barrier filter B2 into the optical path of the observing and photographing optical system 2.

Thus, either of the filters E2 and B2 is inserted into the optical path.

By the way, usually, the focusing of the observing and photographing optical system 2 with respect to the fundus is carried out with only the exciter filter E2 being inserted in the optical path of the illuminating optical system 1 beforehand.

When completing the focusing, the photographic switch 41 is turned on, and then the arithmetic and control circuit 40 actuates the solenoid S4 thereby inserting the barrier filter B2 into the optical path of the observing and photographing optical system 2.

After that, the arithmetic and control circuit 40 causes the halogen lamp 4 to stop or lower the emission by means of the emission control circuit 55 and causes the xenon lamp 6 to emit light in order to photograph the fundus.

Infra-red excitation light of the photographic illumination light emitted by the xenon lamp 6 is projected onto the fundus via the exciter filter E2 and the illuminating optical system 1. The infra-red excitation light excites the ICG included in the vein of the fundus, and thereby infra-red fluorescence (infra-red fluorescent rays) different in wavelength from the illumination light is emitted from the ICG.

The infra-red fluorescence emitted from the fundus is guided to the area CCD 74a of the television camera 74 for infra-red photography via the optical members ranging from the objective lens 17 to the field lens 73 and forms an infra-red fluorescent image thereon. The infra-red fluorescent image is then displayed on the screen of the color liquid crystal monitor 60 via the arithmetic and control circuit 40.

Mydriasis Mode (1) Visible Color Observation and Photography

When a mydriasis mode, i.e., a visible color observation and photography mode instead of the non-mydriasis mode mentioned above is selected by the photographic mode selecting switch 42, the arithmetic and control circuit 40 actuates the solenoid 32 to extract all the filters from the optical paths if the filters are inserted therein, and then illumination light of the halogen lamp 4 is projected onto the eye.

Light reflected by the fundus Ef is guided to the field lens 22 via the objective lens 17, the focusing lens 19, the image-formation lens 20, the dichroic mirror 70, the mirror 21, the mask 36 and forms a color image of the fundus thereon. The color fundus image formed on the field lens 22 is conveyed to the area CCD 30a of the television camera 30 for color photography via the mirror 23 and the relay lens 24 and, in real time, is displayed on the screen of the color liquid crystal monitor 60 via the arithmetic and control circuit 40.

In this state, the operator carries out the alignment and focusing of the observing and photographing optical system 2 with respect to the fundus.

When the alignment and focusing are completed, the photographic switch 41 is turned on, and then the arithmetic and control circuit 40 causes the halogen lamp 4 to stop or lower the light emission and causes the xenon lamp 6 to emit light. The illumination light emitted by the xenon lamp 6 is projected onto the fundus via the illuminating optical system 1.

Visible light reflected by the fundus is guided to the area CCD 30a of the television camera 30 for visible photography via the optical members ranging from the objective lens 17 to the relay lens 24 and forms a color image of the fundus thereon. The color fundus image formed on the area CCD 30a is then displayed in the form of a color image on the screen of the color liquid crystal monitor 60 via the arithmetic and control circuit 40.

(2) Visible Fluorescent Photography

In the case of visible fluorescent photography, while focusing is carried out with respect to the fundus, FAG (fluorescein) which is a fluorescent agent is injected into a vein of the subject.

Before carrying out the focusing, the visible fluorescence photographic mode is first selected by the photographic mode selecting switch 42, and then the exciter switch 44 is pushed. Thereby, the arithmetic and control circuit 40 actuates the driving circuit 51 to drive the solenoid S1 and insert the exciter filter E1 into the optical path.

Likewise, when the barrier switch 46 is pushed, the arithmetic and control circuit 40 actuates the driving circuit 53 to drive the solenoid S3 and insert the barrier filter B1 into the optical path of the observing and photographing optical system 2.

Thus, either of the filters E1 and B1 is inserted into the optical path.

By the way, usually, the focusing of the observing and photographing optical system 2 with respect to the fundus is carried out with only the exciter filter E2 being inserted in the optical path of the illuminating optical system 1 beforehand.

When the focusing is completed, the photographic switch 41 is turned on, and then the arithmetic and control circuit 40 actuates the solenoid S3 thereby inserting the barrier filter B1 into the optical path of the observing and photographing optical system 2. After that, the arithmetic and control circuit 40 causes the xenon lamp 6 to emit light in order to photograph the fundus.

Visible fluorescent rays of light emitted from the vein of the fundus are guided to the area CCD 30a via the barrier filter B1, and then an image of the vein of the fundus formed by the visible fluorescent rays is displayed in the form of a monochromatic image on the screen of the color liquid crystal monitor 60.

As mentioned above, the ophthalmologic apparatus according to the present invention can combine and perform the functions of the mydriasis type of fundus camera and of the non-mydriasis type of fundus camera by mounting the color liquid crystal monitor 60 in the camera body. Further, the structure of the ophthalmologic apparatus can be made simple because the color liquid crystal monitor 60 displays images of the fundus in mydriasis and of the fundus in non-mydriasis, and accordingly, a finder optical system is omitted. In the mydriasis type of fundus camera in which the fundus only in mydriasis is observed and photographed, the finder optical system (finder observation optical system) is required because the fundus must be observed in colors.

In the above embodiment, using the exciter filter E2, the observations of the fundus are made in the mydriasis mode and the visible color photography is performed. Instead, the following may be adopted: A visible cut-off filter 56 is insertably and retractably disposed between the condenser lens 5 and the xenon lamp 6 of the optical system 1 shown in FIG. 1. In the non-mydriasis mode, the filters E1, E2, B1, and B2 are extracted from the optical paths and, instead, the visible cut-off filter 56 is inserted into the optical path. Only infra-red light emitted by the halogen lamp 4 is guided to the fundus via the cut-off filter 56 and the illuminating optical system 1. The fundus is observed with the infra-red light, and thereafter the color photography of the fundus is performed by emitting light from the xenon lamp 6.

Further, a fundus camera exclusively functioning as a non-mydriasis type may be used in which the filters E1, E2, B1, and B2 are omitted and, instead, the cut-off filter 56 is provided.

Since the ophthalmologic apparatus according to the present invention is constructed such that black-and-white fundus images generated by infra-red photography and color fundus images generated by color photography are displayed on the image displaying device mounted in the main body of the ophthalmologic apparatus, an empty space obtained by avoiding use of a color TV monitor that is separated from the body can be effectively utilized and, in addition, harmful illumination light caused by the separated monitor can be extinguished.

An image of the fundus being observed during the alignment is displayed either in a monochrome or in colors on the screen of the monitor. Further, in non-mydriasis, a fundus image being observed during the alignment is displayed in the form of a monochromatic motion image, whereas a fundus image obtained when photographed is displayed in the form of a color still image. Therefore, it is easy to determine whether a displayed fundus image is an image of the fundus obtained when aligning or when photographing.

Further, in order to record a fundus image, a light source for observation which emits stationary light may be used when picking up a motion image of the fundus.

What is claimed is:

1. An ophthalmologic apparatus comprising:

an illuminating optical system for simultaneously or alternatively projecting visible or infra-red light onto a subject's eye;

a color electronic image pickup device sensitive to visible light;

an infra-red electronic image pickup device sensitive to infra-red light;

a color photographic optical system for guiding visible light from said eye to said color electronic image pickup device to form a color ophthalomologic image;

an infra-red photographic optical system for guiding infra-red light from said eye to said infra-red electronic image pickup device to form an infra-red ophthalmologic image;

a color image displaying device mounted in said camera body and displaying in accordance with video signals delivered from either of the color or infra-red electronic image pickup devices either of the color or the infra-red ophthalmologic images; and a control circuit for determining which of said video signals are input to said color image displaying device, so that either of the color or the infra-red ophthalmologic images is displayed on said color image displaying device.

2. An ophthalmologic apparatus according to claim 1, wherein said control circuit controls said illuminating optical system to project infra-red light onto said eye when said ophthalmologic apparatus is actuated, thereafter guiding infra-red light reflected by said eye to said infra-red electronic image pickup device to form the infra-red ophthalmologic image thereon which is displayed on said color image displaying device.

3. An ophthalmologic apparatus according to claim 2, wherein said illuminating optical system comprises an illuminating observation light source which emits infra-red light and an infra-red exciter filter which is inserted into an optical path by a first driving device controlled by said control circuit and which transmits infra-red light for infra-red fluorescence excitation.

4. An ophthalmologic apparatus according to claim 2, wherein said control circuit controls said illuminating optical system to project visible light onto said eye when a photographic switch is turned on, an alignment image being formed by the infra-red light and being displayed on said color image displaying device, thereafter guiding visible light reflected by said eye to said color electronic image pickup device via said color photographic optical system to form the color ophthalmologic image thereon which is displayed on said color image displaying device.

5. An ophthalmologic apparatus according to claim 3, wherein said control circuit stops or lessens light emission of said illuminating observation light source when said photographic switch is turned on, and said control circuit causes the first driving device to retract the exciter filter from the optical path, said control circuit thereafter actuating a xenon lamp to generate and project said visible light onto said eye to be reflected by said eye to said color electronic image pickup device via said color photographic optical system to form the color ophthalmologic image formed on said color electronic image pickup device, the color ophthalmologic image being displayed on said color image displaying device.

6. An ophthalmologic apparatus according to claim 4 or 5, wherein said illuminating optical system includes an illuminating photography light source which emits visible light and a visible exciter filter which is inserted into the optical path by a second driving device controlled by said control circuit and which transmits visible light for visible fluorescence excitation.

7. An ophthalmologic apparatus according to claim 1, wherein said color image displaying device is a color liquid crystal monitor which is forward and backward tiltably mounted in a back of said camera body and is tilted forward and backward by a monitor driving device controlled by said control circuit.

8. An ophthalmologic apparatus according to claim 7, wherein said monitor driving device is a pulse motor.

9. An ophthalmologic apparatus comprising:

an illuminating optical system for simultaneously or alternately projecting visible or infra-red light onto a subject's eye;

a color electronic image pickup device sensitive to visible light;

an infra-red electronic image pickup device sensitive to infra-red light;

a color photographic optical system for guiding visible light from said eye to said color electronic image pickup device to form a color ophthalmologic image;

an infra-red photographic optical system for guiding infra-red light from said eye to said infra-red electronic image pickup device to form an infra-red ophthalmologic image;

a color image displaying device mounted in said camera body and displaying in accordance with video signals delivered from either of the color or the infra-red electronic image pickup devices either of the color or the infra-red ophthalmologic images; and a control circuit for determining which of said video signals are input to said color image displaying device, and for causing said color image displaying device to display either of the color or the infra-red ophthalmologic images in monochrome.

10. An ophthalmologic apparatus according to claim 1 or 9, wherein said control circuit causes said illuminating optical system to emit fluorescent light and causes said color image displaying device to display a fluorescent image formed by fluorescent light reflected from said eye in monochrome during fluorescent photography of said eye.

11. An ophthalmologic apparatus according to claim 1 or 9, wherein said control circuit causes said color image displaying device to display an alignment image of said eye formed by light reflected from said eye during alignment of said ophthalmologic apparatus.

* * * * *